United States Patent
Bashan et al.

(10) Patent No.: US 11,629,327 B2
(45) Date of Patent: Apr. 18, 2023

(54) SYSTEM AND METHOD FOR GROWING ALGAE

(71) Applicant: Vaxa Technologies Ltd, Rosh Pinna (IL)

(72) Inventors: Ohad Bashan, Sde Varburg (IL); Oded Bashan, Rosh Pina (IL); Stephen Drummey, North Easton, MA (US)

(73) Assignee: VAXA TECHNOLOGIES LTD, Rosh Pinna (IL)

( * ) Notice: Subject to any disclaimer, the term of this patent is extended or adjusted under 35 U.S.C. 154(b) by 730 days.

(21) Appl. No.: 16/487,854

(22) PCT Filed: Feb. 20, 2018

(86) PCT No.: PCT/IL2018/050187
§ 371 (c)(1),
(2) Date: Aug. 22, 2019

(87) PCT Pub. No.: WO2018/154565
PCT Pub. Date: Aug. 30, 2018

(65) Prior Publication Data
US 2020/0231925 A1    Jul. 23, 2020

Related U.S. Application Data

(60) Provisional application No. 62/462,372, filed on Feb. 23, 2017.

(51) Int. Cl.
*B01F 35/22*    (2022.01)
*C12M 1/36*    (2006.01)
(Continued)

(52) U.S. Cl.
CPC .......... *C12M 41/48* (2013.01); *B01F 23/231* (2022.01); *B01F 23/29* (2022.01);
(Continued)

(58) Field of Classification Search
CPC .. C12Q 3/00; C12M 1/36; B01F 23/23; B01F 23/29; B01F 35/22
See application file for complete search history.

(56) References Cited

U.S. PATENT DOCUMENTS

7,997,025 B1    8/2011  Masse
10,336,795 B2   7/2019  Brain et al.
(Continued)

FOREIGN PATENT DOCUMENTS

CN    102597211    7/2012
CN    106434283    2/2017
(Continued)

OTHER PUBLICATIONS

English translation of KR20090055169A, Lee Choul Gyun; Date Published Jun. 2, 2009.*
(Continued)

*Primary Examiner* — Walter D. Griffin
*Assistant Examiner* — Cameron J Allen
(74) *Attorney, Agent, or Firm* — Pearl Cohen Zedek Latzer Baratz LLP

(57) ABSTRACT

An algae cultivation system may include: a plurality of panels within a cultivation container, positioned along a first axis perpendicular to the gravitational force, wherein a cultivation volume is created between each pair of panels, and wherein the cultivation volumes are fluidly coupled so as to allow horizontal flow therebetween along the first axis; at least one first sparger, to distribute a first fluid into the container at a first operating flow rate; at least one second sparger, to distribute a second fluid into the container at a second operating flow rate; and at least one controller, to control the first operating flow rate and the second operating flow rate. The first operating flow rate may be adapted to allow turbulent mixing the algae in the cultivation container, (Continued)

and the second operating flow rate may be adapted to allow assimilation of materials in a liquid in the cultivation container.

17 Claims, 3 Drawing Sheets

(51) Int. Cl.
 C12M 1/00 (2006.01)
 C12M 1/06 (2006.01)
 C12M 1/34 (2006.01)
 B01F 23/20 (2022.01)
 B01F 23/231 (2022.01)
 B01F 35/21 (2022.01)
 B01F 35/221 (2022.01)
 B01F 101/44 (2022.01)

(52) U.S. Cl.
 CPC ...... B01F 35/2115 (2022.01); B01F 35/2211 (2022.01); C12M 23/22 (2013.01); C12M 27/02 (2013.01); C12M 31/00 (2013.01); C12M 41/06 (2013.01); C12M 41/12 (2013.01); *B01F 2101/44* (2022.01)

(56) References Cited

U.S. PATENT DOCUMENTS

| | | | |
|---|---|---|---|
| 2009/0047722 A1* | 2/2009 | Wilkerson | C12M 31/10 |
| | | | 435/257.1 |
| 2010/0162621 A1 | 7/2010 | Seebo | |
| 2010/0323436 A1 | 12/2010 | Lee | |
| 2012/0107792 A1* | 5/2012 | Babbitt | C12M 23/36 |
| | | | 435/3 |
| 2012/0115217 A1 | 5/2012 | Chou | |
| 2013/0140425 A1 | 6/2013 | Chou | |
| 2013/0146741 A1 | 6/2013 | Chou | |
| 2015/0210970 A1 | 7/2015 | Hellingwerf et al. | |
| 2016/0289620 A1 | 10/2016 | Mazur | |
| 2017/0145361 A1 | 5/2017 | Bergmann et al. | |

FOREIGN PATENT DOCUMENTS

| | | |
|---|---|---|
| DE | 102010037116 | 2/2012 |
| JP | H07 246086 A | 2/1990 |
| JP | 2010-0511411 | 4/2010 |
| KR | 20090055169 A * | 6/2009 |
| RU | 2148635 C1 | 5/2000 |
| RU | 2165973 C2 | 4/2001 |

OTHER PUBLICATIONS

International Search Report for PCT Application No. PCT/IL2018/050187, dated May 16, 2018.
European Search Report for App. No. EP18758344.8 dated Nov. 19, 2020.
Russian Office Action for App. No. 2019129562 dated Jul. 5, 2021.
Jian Li et al., "Design and characterization of a scalable airlift flat panel photobioreactor for microalgae cultivation", *Journal of Applied Phycology*, vol. 27, pp. 75-86, May 22, 2014.
Iain Ratchford and Howard Fallowfield, "Performance of a flat plate, air-lift reactor for the growth of high biomass algal cultures", Journal of Applied Phycology, vol. 4, No. 1, pp. 1-9, Mar. 1992.
Lin-Lin Wang , et al., "A novel flat plate algal bioreactor with horizontal baffles: structural optimization and cultivation performance", *Bioresource Technology*, vol. 164, pp. 20-27, 2014.
Niels T. Eriksen el al., "Dual sparging laboratory-scale photobioreactor for continuous production of microalgae", *Journal of Applied Phycology*, vol. 10, pp. 377-382, May 21, 1998.
Office Action from Japanese Application No. 2019-545995, dated Dec. 7, 2021.
Office Action for Chinese App. No. 201880026643, dated Sep. 2, 2022.

* cited by examiner

```
┌─────────────────────────────────────────────────────────┐
│ Controlling at least one first sparger to distribute a  │
│ first fluid into the container at a first operating flow│
│                         rate                            │
└─────────────────────────────────────────────────────────┘
 201
                            ▼
┌─────────────────────────────────────────────────────────┐
│ Controlling at least one second sparger to distribute   │
│  a second fluid into the container at a second          │
│             operating flow rate                         │
└─────────────────────────────────────────────────────────┘
 202
                            ▼
┌─────────────────────────────────────────────────────────┐
│ Controlling a temperature module to manage the          │
│ temperature of fluids within the cultivation            │
│                    container                            │
└─────────────────────────────────────────────────────────┘
 203
                            ▼
┌─────────────────────────────────────────────────────────┐
│ Controlling fluid flow between at least two             │
│ cultivation volumes created between pairs of panels     │
│ positioned within the cultivation container, along an   │
│ axis perpendicular to the gravitational force           │
└─────────────────────────────────────────────────────────┘
 204
```

Fig. 2

SYSTEM AND METHOD FOR GROWING ALGAE

CROSS-REFERENCE TO RELATED APPLICATIONS

This application is a National Phase Application of PCT International Application No. PCT/IL2018/050187, International Filing Date Feb. 20, 2018, claiming the benefit of U.S. Patent Application No. 62/462,372, filed Feb. 23, 2017, which is hereby incorporated by reference in its entirety.

FIELD OF THE INVENTION

The present invention generally relates to algae growth. More particularly, the present invention relates to systems and methods for enhancing algae growth.

BACKGROUND OF THE INVENTION

In recent years, algae cultivation in artificial conditions with bio-reactors (e.g., with bubble columns) has become increasingly common, for instance in order to produce biomass. For optimal conditions and accelerated growth, the algae (or microalgae) are supplied with $CO_2$-enriched air bubbles and illumination (either artificial illumination, or from sunlight). About 50% of algal biomass is carbon, obtained by fixing $CO_2$ photosynthetically, where carbon dioxide needs to be dissolved into the culture in a liquid phase. In phototropic algae cultivation systems the major inputs (or macro-nutrients) for growth are light, $CO_2$, nutrients (such as Nitrogen, Phosphorus, etc.), and water turbulently mixed in order to distribute these resources to individual algae cultivation cells.

Further to the above, the mixing is required for achieving high algae concentration in the bio-reactors. Efficient mixing can increase the cells' light exposure, by reducing the degree of mutual shading (made by neighboring cells) and minimizing photo-inhibition. The efficient mixing can move the cells close to the illuminated surface to obtain a photon input, and then away from it, in order to give the photon-saturated cells the opportunity to absorb the light energy for photosynthesis, before the cells are exposed to the light again. Since ultra-high cell concentrations requires the usage of powerful light sources, inadequate mixing might result with over-exposure to high doses of photons in some cells, and severe damage due to photo-inhibition in other cells. Gas sparging (mainly air or Nitrogen enriched with $CO_2$) is commonly used in photo-bioreactors (PBRs) in order to create the required mixing. The rising motion of the bubbles creates mixing tangential to the flow direction.

Microalgae can be photographically grown in many types of systems, such as flat panel photo-bio-reactors having efficient light capture and utilization, and high surface area-to-volume ratio. Light sources for algae growth can be any type of visible light in a wavelengths range of about 400-700 nm. Light emitting diodes (LEDs) have the capability of providing light of specific wavelengths, for example in the visible light (e.g., blue and/or red) wavelength range.

For most species of microalgae, both the growth rate and the composition of the biomass are directly affected by the temperature of the culture. For example, in outdoor flat panel systems, there are significant swings in temperature between night (i.e., due to darkness) and day (i.e., due to heat from the sunlight), where these temperature swings are exacerbated by the small volumes and high light exposure of the algae growth systems.

Some flat thin film photo-bio-reactor systems consist of modular, stand-alone units with limited volume per panel (or bio-reactor). Such panels do not have horizontal flow therebetween, and the flow is vertical to allow the bubbles to go up as some end up outside of the tank. Therefore, large-scale installations consist of many such production units. This presents significant capital, operational and maintainability challenges due to a significantly large amount of sample and control (e.g., pH, temperature, nutrient level, harvest ports, etc.) points. Moreover, in large-scale installations with many different separate units, there are inevitable slight differences in the chemical and environmental conditions within each panel (or bio-reactor), and the resulting biological processes within each panel. Therefore, each of these panels must be managed separately, and can have varying production rates from one panel to another.

Furthermore, some thin film algae cultivation systems have far less thermal mass than other non-thin film algae cultivation systems, and therefore the temperature of the culture medium can reach high levels due to exposure to either artificial or natural light sources. These high temperatures can be counterproductive for optimizing growth rate and composition and/or can even be fatal to the algae culture.

SUMMARY OF EMBODIMENTS OF THE INVENTION

Some aspects of the invention may be directed to an algae cultivation system. The system may include: a plurality of panels within a cultivation container, positioned along a first axis perpendicular to the gravitational force, wherein a cultivation volume is created between each pair of panels, and wherein the cultivation volumes are fluidly coupled so as to allow horizontal flow therebetween along the first axis; at least one first sparger, to distribute a first fluid into the container at a first operating flow rate; at least one second sparger, to distribute a second fluid into the container at a second operating flow rate; and at least one controller, to control the first operating flow rate and the second operating flow rate. In some embodiments, the at least one controller may also control fluid flow between at least two cultivation volumes. In some embodiments, the first operating flow rate may be adapted to allow turbulent mixing the algae in the cultivation container, and wherein the second operating flow rate is adapted to allow assimilation of materials in a liquid in the cultivation container. In some embodiments, the panels may be transparent.

In some embodiments, the system may further include at least one sensor, to measure at least one parameter within the container and the controller may further be configured to control the first operating flow rate and the second operating flow rate based on measurements received from the at least one sensor. In some embodiments, the measured parameter is selected from the group consisting of algae density, temperature, PH, illumination intensity and pressure within the container.

In some embodiments, the system may further include a temperature sensor and a temperature module that may be configured to manage the temperature of fluids within the cultivation container based on temperature measurements received from the temperature sensor.

Some other aspects of the invention may be directed to an algae cultivation system. The system may include: a plurality of panels within a cultivation container, positioned along a first axis perpendicular to the gravitational force, a cultivation volume may be created between each pair of panels, and the cultivation volumes may be fluidly coupled therebetween so as to allow horizontal flow along the first axis. The system may further include at least one first sparger, to distribute a first fluid into the container; at least one illumination unit for each panel, to illuminate adjacent cultivation volumes; and at least one controller, to control the flow rate of the first fluid, and to control fluid flow between at least two panels. In some embodiments, the flow rate of the first fluid may be adapted to allow turbulent mixing the algae in the cultivation container, and the controller may be configured to control the at least one illumination unit.

In some embodiments, the system may further include at least two illumination units for at least one panel, such that at least one illumination unit is controlled to illuminate with a different intensity than another illumination unit. In some embodiments, the system may further include at least one sensor, to measure at least one parameter within the container and the controller may further be configured to control the flow rate of the first fluid, and the fluid flow between at least two panels based on measurements received from the at least one sensor.

In some embodiments, the system may further include a temperature sensor; and a temperature module, configured to manage the temperature of fluids within the cultivation container based on input from the temperature sensor.

In some embodiments, the system may further include at least two illumination units for at least one panel, such that at least one illumination unit is controlled to illuminate with a different wavelength than another illumination unit. In some embodiments, the system may further include at least one second sparger controlled by the at least one controller, to distribute a second fluid into the container at a second operating flow rate based on the at least one measured parameter, the second operating flow rate may be adapted to allow assimilation of materials in a liquid in the cultivation container.

In some embodiments, each panel comprises at least one sensor, to measure at least one parameter within an adjacent cultivation volume.

Some additional aspects of the invention may be directed to a method of growing algae in a cultivation container. The method may include: controlling at least one first sparger to distribute a first fluid into the container at a first operating flow rate; controlling at least one second sparger to distribute a second fluid into the container at a second operating flow rate; and controlling fluid flow between at least two cultivation volumes created between pairs of panels positioned within the cultivation container, along an axis perpendicular to the gravitational force. In some embodiments, the first operating flow rate may be adapted to allow mixing the algae in the cultivation container, and the second operating flow rate may be adapted to allow assimilation of materials in a liquid in the cultivation container.

Some embodiments may include measuring temperature within the container with at least one sensor, such that the fluid flow between at least two cultivation volumes is based on the measured temperature. Some embodiments may include controlling a temperature module to manage the temperature of fluids within the cultivation container. Some embodiments may include illuminating each cultivation volume with at least one illumination unit.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2 shows a flow chart of a method of growing algae in a cultivation container, according to some embodiments of the invention.

Figure 1A:
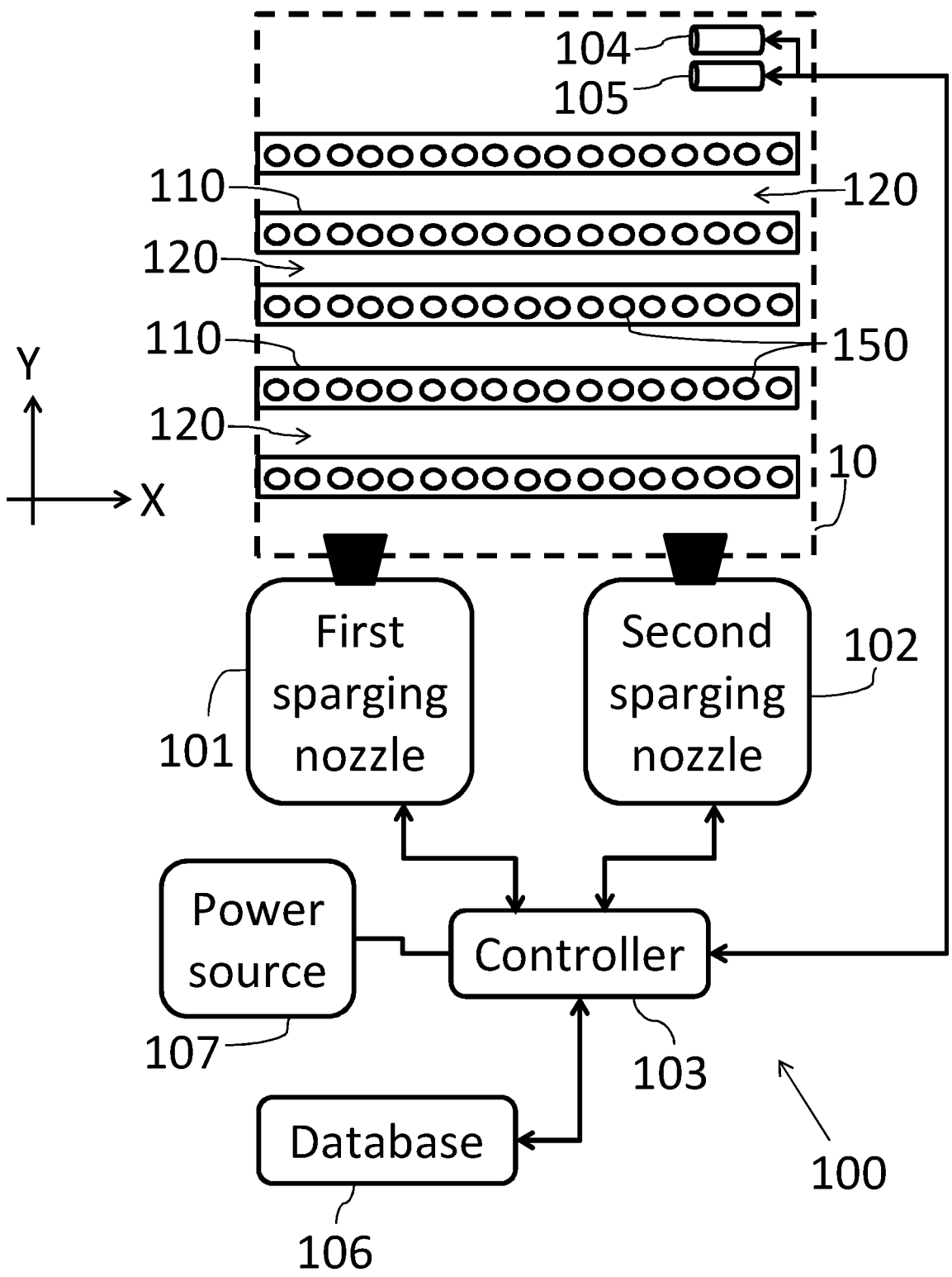
FIG. 1A schematically illustrates a block diagram of an algae cultivation system, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of embodiments of the invention. However, it will be understood by those skilled in the art that the present invention may be practiced without these specific details. In other instances, well-known methods, procedures, and components have not been described in detail so as not to obscure the present invention.

Reference is now made to FIG. 1A, which schematically illustrates a block diagram of an algae cultivation system 100, according to some embodiments of the invention. It should be noted that the direction of the arrows in FIG. 1A may indicate the direction of information flow. Cultivation system 100 may include at least two panels 110 within a water filled cultivation container 10. For example, the panels 110 may be positioned along a first axis (indicated 'X') that is perpendicular to the gravitational force and along a second axis (indicated 'Y'). In some embodiments, a cultivation volume 120 may be created between each pair of panels 110, whereby the cultivation volumes 120 may be fluidly coupled so as to allow horizontal flow therebetween along the first axis (indicated 'X'). For example, each panel 110 may include a passage to allow flow of a fluid containing a culture (e.g., algae culture) between adjacent cultivation volumes 120.

It should be noted that such horizontal (recirculating) flow of algae culture within multiple linked panels 110 and/or cultivation volumes 120, may thereby create a single large volume within cultivation container 10 by linking cultivation units (e.g., a cultivation volume 120 between two panels 110) together. Such a single large volume may prevent large-scale management of separate cultivation units, and allow to increase the biological productivity and homogenization of the conditions within container 10. In some embodiments, the panels 110 may include a transparent material, so as to allow light passage so as to illuminate the adjacent cultivation volumes 120.

According to some embodiments, cultivation system 100 may include at least one first sparger 101 with a plurality of nozzles, to distribute a first predetermined fluid (e.g., air bubbles) into the algae cultivation container 10 (e.g., a bio-reactor with flat thin-films) at a first operating flow rate so as to allow mixing therein. Cultivation system 100 may further include at least one second sparger 102 with a plurality of nozzles, to distribute a second predetermined fluid (e.g., including gas bubbles with $CO_2$ and/or dissolved phosphorus for mass transfer) into the container 10 at a second operating flow rate.

In some embodiments, cultivation system 100 may include at least one controller 103, to control the first operating flow rate and the second operating flow rate. The flowrate may be controlled by providing the fluids (e.g., gases) to the first sparger and the second sparger at a first pressure and a second pressure correspondingly. A first supply line may supply the first fluid (e.g., air) at the first pressure and controller 103 may control a compressor to change the pressure of the provided first fluid. A second supply line may supply the second fluid (e.g., $CO_2$) at the second pressure and controller 103 may control a compressor to change the pressure of the supplied second fluid. Additionally or alternatively the first and/or second supply lines may include controllable valve (e.g., a shutter, a tap, and the like) adopted to change the capacity of the fluid provided to each sparger. Controller 103 may control the capacity of the first and/or second fluids by controlling a first and/or second controllable valves.

According to some embodiments, at least one nozzle of first sparger 101 and second sparger 102 may distribute fluid into cultivation container 10 based on a request from at least one controller 103, as further described hereinafter. In some embodiments, first operating flow rate may be based on the second operating flow rate. In some embodiments, at least one of the first operating flow rate and the second operating flow rate is predetermined. In some embodiments, the at least one controller 103 may also control fluid flow between at least two cultivation volumes 120.

In some embodiments, the first operating flow rate may be adapted to allow turbulent mixing of the algae in cultivation container 10. In some embodiments, the second operating flow rate may be adapted to allow mass transfer and/or assimilation of materials in a liquid in cultivation container 10. In some embodiments, the first operating flow rate is higher than the second operating flow rate. In some embodiments, the first operating flow rate of at least one nozzle of first sparger 101 (e.g., 100 millimeters/minute) may be different from the second operating flow rate of at least one nozzle of second sparger 102 (e.g., 5 millimeters/minute).

In some embodiments, second predetermined fluid may include gas bubbles with over 30% $CO_2$ concentration. According to some embodiments, the source for at least one first predetermined fluid and second predetermined fluid may be external to cultivation system 100, for example geothermal power stations may provide a source of dissolved Carbon and/or Sulfur for the second predetermined fluid.

In some embodiments, cultivation system 100 may further include at least one sensor 104 and 105 (e.g., temperature sensor 104) in communication with controller 103 and configured to detect at least one parameter within cultivation container 10. For example, at least one sensor 105 may detect at least one of algae density, pH levels, temperature illumination intensity and pressure conditions within cultivation container 10. In some embodiments, at least one sensor 104 or 105 may also detect parameters external to cultivation container 10, for example measuring mass flow of the gas emissions from cultivation container 10 to determine amount of substance that was absorbed in the algae cells by subtracting the emitted amount from the amount inserted into the container (e.g., by second sparger 102). In some embodiments, at least one second sparger 102 may distribute the second fluid into the container at the second operating flow rate based on the at least one parameter measured by the at least one sensor 104 or 105. In some embodiments, more than one sensor may be located within cultivation container 10. For example, a temperature sensor 104 may located at exit 131 illustrated in FIG. 1B and a pH sensor 105 may be located elsewhere in container 10.

Figure 1B:
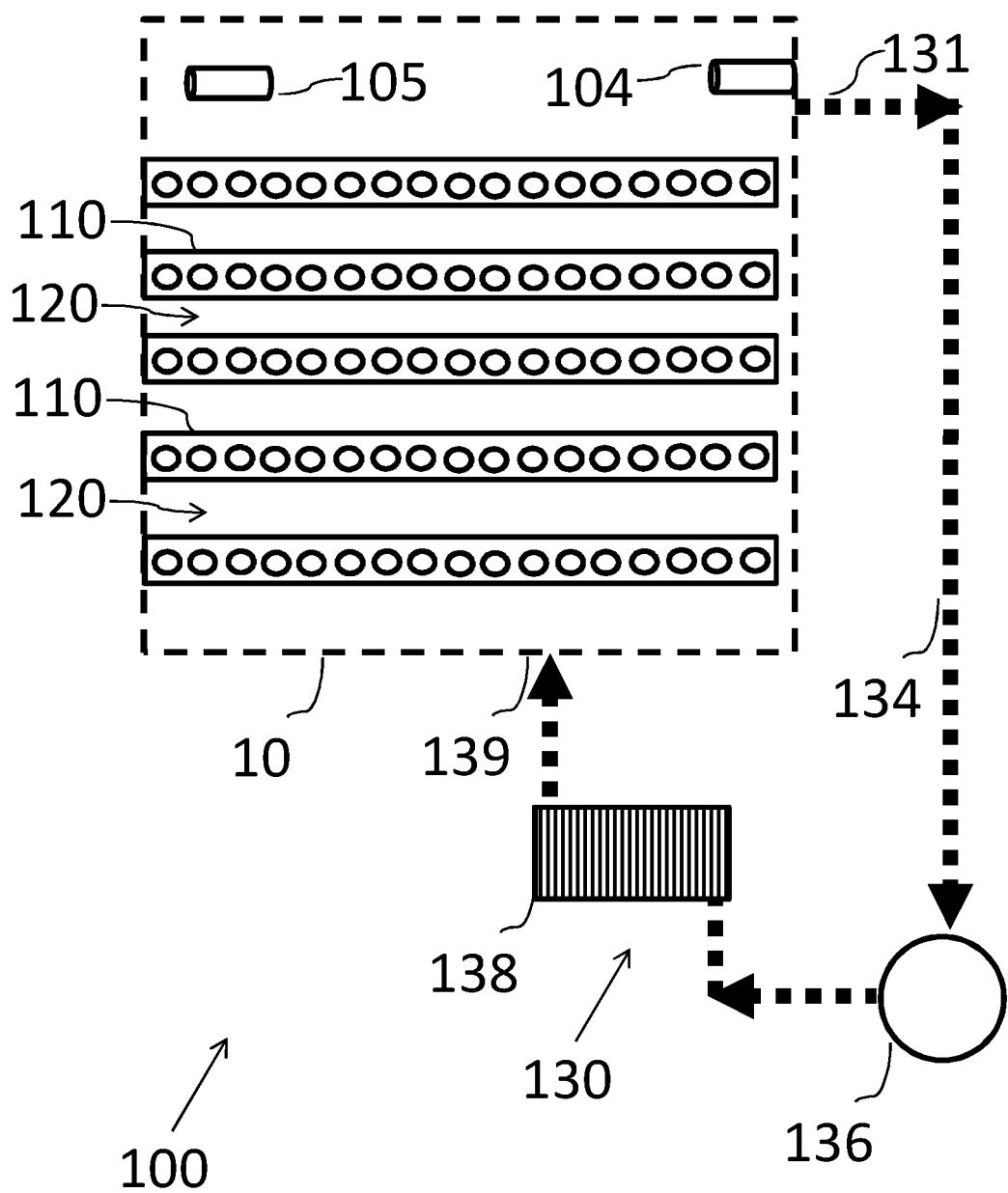
FIG. 1B schematically illustrates a temperature module included in the algae cultivation system, according to some embodiments of the invention.

Reference is now made to FIG. 1B which is an illustration of a temperature module included in a cultivation system according to some embodiments of the invention. In some embodiments, cultivation system 100 may further include at least one temperature module 138 configured to manage the temperature of fluids within the cultivation container 10, for example, based on input from the at least one temperature sensor 104. In some embodiments, a circulating system 130 may include a circulating pipe 134 for circulating the fluid containing the culture (e.g., water with algae culture) from exit 131 (e.g., located at the upper portion of container 10) towards entrance 139 (e.g., located at the bottom of container 10). The fluid containing the culture may be circulated using a pump 136 via at least one temperature module 138. At least one temperature module 138 may be any unit that may provide/extract heat to/from the fluid containing the culture. For example, at least one temperature module 138 may include at least one of: a heat exchanger, a heating element, a cooling water pipe, a tank comprising a cooling/heating medium and the like. In some embodiments, the fluid containing the culture may be circulated via at least one temperature module 138 by pump 136 and pipe 134. Additionally or alternatively, at least a portion of container 10 may be in direct contact with at least one temperature module 138 (e.g., a tank or a heat exchanger) for directly conveying heat from/to the walls of container 10.

It should be noted that by allowing the fluid to flow in a circular flow in container 10, it may be possible to obtain average culture composition that may be monitored (e.g., monitoring pH level of the fluid) from a single monitoring point, with thermal management of a large system at a single access point (e.g., for heat exchange processes). In some embodiments, fluid may be circulated between several fluidly coupled algae cultivation containers 10, with central monitoring. In some embodiments, the amount of heat extracted/provided to the fluid containing the culture may be controlled based to temperature reading from at least one temperature sensor 104. In some embodiments, controller 103 may control at least one of: the flow of the fluid containing the culture (e.g., by controlling pump 136), the temperature/flow of a cooling liquid provided to at least one temperature module 138 and the like.

Referring back to FIG. 1A, in some embodiments, cultivation system 100 may further include at least one database 106 (or memory unit) configured to store algorithms for operation of controller 103, for instance database of operating rates for each nozzle and/or each sparger and/or control of temperature module 138. In some embodiments, cultivation system 100 may further include a power source 107 coupled to controller 103 and configured to provide electrical power to the electrical components of cultivation system 100. Power source 107 may provide power to a first and second valves of the first and second spargers for controlling the first and second flow rates, may provide power to pump 136 for controlling the amount of heat extracted/provided to the fluid containing the culture and the like.

In some embodiments, data gathered by at least one sensor 105 may be analyzed by controller (or processor) 103 to detect if an attribute exceeds a predetermined threshold, for instance threshold for pH level and/or temperature and/or $CO_2$ concentration within the container 10. In case that conditions within cultivation container 10 (e.g., as detected by pH sensor 105) exceed at least one threshold, then controller 103 may operate the first valve of the first sparger 101 and/or at least the second valve of second sparger 102 to provide different flow rates. For example, if the pH level exceeds a predetermined threshold indicating that the culture (e.g., Algae) within container 10 is not provided with a sufficient dissolved carbon in the water, the second valve may be opened/extended to provide or increase the amount of $CO_2$ supplied to container 10 via second sparger 102. In another example, if pH levels at various placed in container 10 vary in a predetermined threshold indicating an unbalanced provision of $CO_2$, the amount of air provided by, for example, sparger 101 may be increased in order to increase the circulation within container 10.

In yet another example, if sensor 104 may detect that temperature in proximity to exit 131 exceeds 50 C (or detecting low pH levels) the controller may cause temperature module 138 to lower temperature within container 10 to ~30 C, by more rapidly circulating (e.g., using pump 136) of the fluid containing the culture via temperature module 138, providing cooler cooling liquid to temperature module 138 and the like. In some embodiments, at least one nozzle of second sparger 102 may operate only upon receiving a signal from sensor 105 or 104 that an attribute exceeds a predetermined threshold, and not operated in a constant rate. In some embodiments, each panel 110 may include at least one sensor 105, to measure at least one parameter within an adjacent cultivation volume.

In some embodiments, each panel 110 in algae cultivation system 100 may include at least one illumination unit 150 (e.g., LED), coupled to controller 103, to illuminate adjacent cultivation volumes 120 within cultivation container 10. In some embodiments, controller 103 may separately control the illumination intensity and illumination periods of each illumination unit 150. In some embodiments, at least one illumination unit 150 may be controlled to illuminate with a different intensity than another illumination unit 150. According to some embodiments, all illumination units 150 may be controlled to change the illumination intensity, either manually or according to preset timing and/or sensed conditions in cultivation container 10, for example, according to the amount of natural light expected at a particular calendric month. In some embodiments, controller 103 may be configured to control the illumination wavelength of the at least one illumination unit 150, for instance with a dedicated illumination module adapted to modify the wavelength of the emitted illumination.

As may be appreciated by one of ordinary skill in the art, illuminated algae cultivation systems do not experience significant daily temperature swings, however the light intensity required for high density algae cultures in some bio-reactor systems may require a high light exposure, and thus a great deal of heat exposure for the cultivation panels as well. It should be noted that algae cultivation system 100 may allow high intensity illumination (e.g., with LEDs) while also allowing control of the temperature within cultivation container 10 (as a large production volume) by homogeneously mixing large volumes of algae culture, that may be flowed through a heat exchange system (e.g., module 138) to provide stable targeted temperatures for optimized biomass production and composition. For example, algae cultivation system 100 with temperature module 138 maintaining a required temperature within container 10 may achieve a daily biomass yield of about 2.8 gram/liter, and/or a daily Omega-3 yield of about 190 milligrams/liter, thereby having a five-fold improvement over other systems, as disclosed herein.

In some embodiments, cultivation system 100 may include at least two illumination units 150 for at least one panel 110, wherein at least one illumination unit 150 may be controlled, by controller 103, to illuminate with a different intensity than another illumination unit 150. In some embodiments, cultivation system 100 may include at least two illumination units 150 for at least one panel 110, wherein at least one illumination unit 150 may be controlled, by controller 103, to illuminate with a different wavelength than another illumination unit 150.

Reference is now made to FIG. 2, which is a flowchart of a method of growing algae in a cultivation container 10, according to some embodiments of the invention. In some embodiments, at least one first sparger 101 may be controlled 201 to distribute a first fluid into the container 10 at a first operating flow rate. In some embodiments, at least one second sparger 102 may be controlled 202 to distribute a second fluid into the container 10 at a second operating flow rate. For example, controller 103 may control at least a first valve and/or a first and/or compressor to supply the first fluid at a first operating flow rate and/or control at least a second valve and/or a second and/or compressor to supply the second fluid at a second operating flow rate.

In some embodiments, a temperature module 138 may be controlled 203 to manage the temperature of fluids within the cultivation container 10. For example, by controlling pump 136 to circulate the fluid containing the culture via temperature module 138 or control the temperature or amount of cooling liquid provided to temperature module 138 (e.g., a heat exchanger). In some embodiments, fluid flow may be controlled 204 between at least two cultivation volumes 120 created between pairs of panels 110 positioned within the cultivation container 10, along an axis perpendicular to the gravitational force, for example, by pump 136.

In some embodiments, the temperature of the fluid containing the culture may be maintained at an optimal level, between a lower and an upper threshold values (e.g., 20-50° C.). Undesired excess heat may be introduced to container 10 form the illumination provided to container 10, a temperature external to container 10 and the like. In some embodiments, temperature within the container may be measured with at least one temperature sensor 104, wherein the fluid flow between at least two cultivation volumes 120 may be based on the measured temperature. For example, if the temperature measured by sensor 104 exceeds a predetermined threshold value (e.g., 50° C.) controller 103 may control pump 136 to rapidly circulate the fluid containing the culture via temperature module 138 in order to reduce the measure temperature to approximately 30° C. In the case that such a reduction of the temperature fails, the culture may be damaged.

In some embodiments, each cultivation volume 120 may be illuminated with at least one illumination unit 150. In some embodiments, at least one parameter may be measured within the container 10 by at least one sensor 105, wherein temperature of fluids within the cultivation container 10 may be managed based on the measured at least one parameter.

Unless explicitly stated, the method embodiments described herein are not constrained to a particular order in time or chronological sequence. Additionally, some of the described method elements can be skipped, or they can be repeated, during a sequence of operations of a method.

Various embodiments have been presented. Each of these embodiments may of course include features from other

The invention claimed is:

1. An algae cultivation system, comprising:
a plurality of panels within a cultivation container, positioned along a first axis perpendicular to the gravitational force, wherein a cultivation volume is created between each pair of panels, and wherein the cultivation volumes are fluidly coupled so as to allow horizontal flow therebetween along the first axis;
at least one first sparger, configured to distribute a first fluid into the container at a first operating flow rate;
at least one second sparger, configured to distribute a second fluid into the container at a second operating flow rate;
at least one illumination unit for each panel, configured to illuminate adjacent cultivation volumes, wherein the at least one illumination unit comprises at least two illumination units for at least one panel, wherein at least one illumination unit is controlled to illuminate with a different intensity and/or a different wavelength than another illumination unit, and
at least one controller, configured to control the first operating flow rate and the second operating flow rate, wherein the at least one controller is also to control fluid flow between at least two cultivation volumes,
wherein the first operating flow rate is adapted to allow turbulent mixing the algae in the cultivation container, and wherein the second operating flow rate is adapted to allow assimilation of materials in a liquid in the cultivation container.

2. The algae cultivation system according to claim 1, further comprising:
at least one sensor, configured to measure at least one parameter within the container and wherein the controller is further configured to control the first operating flow rate and the second operating flow rate based on measurements received from the at least one sensor.

3. The algae cultivation system according to claim 2, wherein the measured parameter is selected from the group consisting of algae density, temperature, PH, illumination intensity and pressure within the container.

4. The algae cultivation system according to claim 1, further comprising:
a temperature sensor; and
a temperature module, configured to manage the temperature of fluids within the cultivation container based on temperature measurements received from the temperature sensor.

5. The algae cultivation system according to claim 1, wherein the panels are transparent.

6. An algae cultivation system, comprising:
a plurality of panels within a cultivation container, positioned along a first axis perpendicular to the gravitational force, wherein a cultivation volume is created between each pair of panels, and wherein the cultivation volumes are fluidly coupled therebetween so as to allow horizontal flow along the first axis;
at least one first sparger, to distribute a first fluid into the container;
at least one illumination unit for each panel, to illuminate adjacent cultivation volumes; and
at least one controller, to control the flow rate of the first fluid, and to control fluid flow between at least two panels,
wherein the flow rate of the first fluid is adapted to allow turbulent mixing the algae in the cultivation container, and wherein the controller is configured to control the at least one illumination unit and
wherein the at least one illumination unit comprises at least two illumination units for at least one panel, wherein at least one illumination unit is controlled to illuminate with a different intensity and/or a different wavelength than another illumination unit.

7. The algae cultivation system according to claim 6, wherein the at least two illumination units are controlled to illuminate with different intensities.

8. The algae cultivation system according to claim 6, further comprising:
at least one sensor, configured to measure at least one parameter within the container and wherein the controller is further configured control the flow rate of the first fluid, and the fluid flow between at least two panels based on measurements received from the at least one sensor.

9. The algae cultivation system according to claim 6, further comprising:
a temperature sensor; and
a temperature module, configured to manage the temperature of fluids within the cultivation container based on input from the temperature sensor.

10. The algae cultivation system according to claim 6, wherein the at least two illumination units are controlled to illuminate with different wavelengths.

11. The algae cultivation system according to claim 6, comprising at least one second sparger controlled by the at least one controller, to distribute a second fluid into the container at a second operating flow rate based on the at least one measured parameter, wherein the second operating flow rate is adapted to allow assimilation of materials in a liquid in the cultivation container.

12. The algae cultivation system according to claim 6, wherein each panel comprises at least one sensor, to measure at least one parameter within an adjacent cultivation volume.

13. A method of growing algae in a cultivation container, the method comprising:
controlling at least one first sparger to distribute a first fluid into the container at a first operating flow rate;
controlling at least one second sparger to distribute a second fluid into the container at a second operating flow rate; and
controlling fluid flow between at least two cultivation volumes created between pairs of panels positioned within the cultivation container, along an axis perpendicular to the gravitational force,
wherein the first operating flow rate is adapted to allow mixing the algae in the cultivation container, and wherein the second operating flow rate is adapted to allow assimilation of materials in a liquid in the cultivation container,
wherein the method further comprises:
illuminating each cultivation volume with at least one illumination unit, wherein the at least one illumination unit comprises at least two illumination units for at least one panel, and
controlling the at least one illumination unit to illuminate with a different intensity and/or a different wavelength than another illumination unit.

14. The method according to claim 13, comprising measuring temperature within the container with at least one sensor, wherein the fluid flow between at least two cultivation volumes is based on the measured temperature.

15. The method according to claim 13, comprising controlling a temperature module to manage the temperature of fluids within the cultivation container.

16. The method according to claim 13, wherein the controlling of the at least one illumination unit comprises controlling of the at least two illumination units to illuminate with different intensities.

17. The method according to claim 13, wherein the controlling of the at least one illumination unit comprises controlling of the at least two illumination units to illuminate with different wavelengths.

* * * * *